United States Patent [19]

O'Meara, Jr. et al.

[11] Patent Number: 4,893,504
[45] Date of Patent: Jan. 16, 1990

[54] METHOD FOR DETERMINING CAPILLARY PRESSURE AND RELATIVE PERMEABILITY BY IMAGING

[75] Inventors: Daniel J. O'Meara, Jr.; Harold J. Vinegar, both of Houston, Tex.

[73] Assignee: Shell Oil Company, Houston, Tex.

[21] Appl. No.: 222,878

[22] Filed: Jul. 22, 1988

Related U.S. Application Data

[62] Division of Ser. No. 881,159, Jul. 2, 1986, abandoned.

[51] Int. Cl.$^4$ .............................................. E21B 49/02
[52] U.S. Cl. ...................................................... 73/153
[58] Field of Search ................... 73/153; 250/253, 255, 250/256, 258; 166/250; 324/303, 376, 377; 378/5, 10

[56] References Cited

U.S. PATENT DOCUMENTS

| | | | |
|---|---|---|---|
| 4,543,821 | 10/1985 | Davis, Jr. | 73/153 |
| 4,562,540 | 12/1985 | Deraney | 250/256 |
| 4,751,646 | 6/1988 | Alger | 73/153 |

Primary Examiner—Robert R. Raevis

[57] ABSTRACT

The present invention provides methods and apparatus for determining relative permeability and capillary pressure employing saturation profile images of fluids in a porous sample obtained by imaging apparatus. The methods employ saturation profiles of a fluid to obtain time and spatial derivatives of the saturation profiles. The methods then employ the time derivatives with measured total superficial velocities to determine individual superficial velocities of the fluids which may then be employed with the spatial derivatives to determine mobility coefficients. The methods of the present invention may also measure the pressures of one fluid and then determine relative permeabilities and capillary pressures for all the fluids in the porous sample.

9 Claims, 2 Drawing Sheets

METHOD FOR DETERMINING CAPILLARY PRESSURE AND RELATIVE PERMEABILITY BY IMAGING

This is a division, of application Ser. No. 881,159, filed July 2, 1986 now abandoned.

BACKGROUND OF THE INVENTION

This invention relates to imaging of materials, and more particularly, relates to imaging materials to determine selected petrophysical properties.

Welge and conventional centrifuge methods for measuring relative permeability of a porous material, as well as the centrifuge method for measuring capillary pressure, all use effluent data to calculate saturations at either the inflow or outflow ends of the sample of material, usually an earthen core sample. On the other hand, the steady-state method for measuring relative permeabilities, as well as the capillary diaphragm and mercury injection methods for measuring capillary pressures, assume uniform saturations in a sample.

In general, the previous prior art methods for measuring relative permeability assume capillary pressure effects are negligible. And, conversely, the prior art capillary pressure methods assume relative permeability effects are negligible. These assumptions, however, are not always satisfied. Such methods, which depend on effluent data are, therefore, incorrect to the extent that the model for reconstructing saturation profiles is influenced by the effect assumed negligible. for example, a problem with the Welge method is that it ignores any capillary end effect. Further, the methods which rely on uniform saturation are incorrect to the extent that the neglected effect prevents obtaining uniform saturations. For example, the low relative permeability of the displaced phase in the capillary diaphragm method can result in inordinately long times to reach uniform saturations.

These and other limitations and disadvantages of prior art are overcome by the present invention and improved methods and apparatus are provided for measuring selected petrophysical properties, such as capillary pressure and/or relative permeability, of a material or fluids therein.

SUMMARY OF THE INVENTION

In a preferred embodiment of the present invention methods and apparatus are provided for measuring selected petrophysical properties, such as capillary pressure and relative permeability, of a material or fluids therein from information obtained by imaging the material and fluids therein. The methods are not limited to any particular type of imaging technique and may be employed with X-ray CT, Nuclear Magnetic Resonance Imaging (NMRI), or linear scanning γ-ray apparatus providing they have sufficient resolution for saturation imaging. This resolution may vary with the objects of the methods; for lower relative permeabilities the resolution must be sufficient to detect and measure smaller changes in saturation.

The methods measure the spatial saturation profile in a sample of a material with an imaging apparatus and uses this profile to calculate the derivative of saturation as a function of location and time in the sample. Also, in accordance with the methods of the present invention, the total superficial velocity of any fluids imbided or injected into the sample (and whose saturation is imaged) may be measured. The time derivatives and total superficial velocity may then be employed to calculate individual superficial velocities of the fluids. The individual superficial velocities may be employed with spatial derivatives to calculate mobility coefficients. The pressures of one fluid may be measured to calculate relative permeabilities and capillary pressures for fluids in the sample from these pressures and mobility coefficients. Thus, the velocities, pressures, spatial saturations, and saturation derivatives may, in accordance with the teachings of the methods of the present invention, be employed to calculate mobility coefficients, mobilities, relative permeability and capillary pressures using Darcy's Law.

The apparatus of the present invention is a sample holder for use in a CT, NMR or other type imaging device having a cylindrical member for containing the sample with two endpieces held in place by clamps. The endpieces conduct fluids into and out of the sample via appropriate openings and the exit endpiece may contain a capillary diaphragm. The cylindrical member may also have openings for pressure taps spaced therealong. The sample holder may be encased in a suitable material to avoid X-ray hardening, or made of non-magnetic materials for NMRI uses.

It is an object of the present invention to provide methods and apparatus for determining the capillary pressure and relative permeability of a material.

It is also an object of the present invention to provide methods and apparatus for determining the capillary pressure of a material.

It is also an object of the present invention to provide methods and apparatus for determining the relative permeability of a material.

It is a further object of the present invention to provide methods and apparatus for determining mobility coefficients of a material.

It is yet a further object of the present invention to provide methods and apparatus for determining the mobilities of fluids in a material.

These and other objects and advantages of the present invention will become apparent from the following detailed description, wherein reference is made to the Figures in the accompanying drawings.

IN THE DRAWINGS

DETAILED DESCRIPTION OF THE PREFERRED EMBODIMENTS

Figure 1:
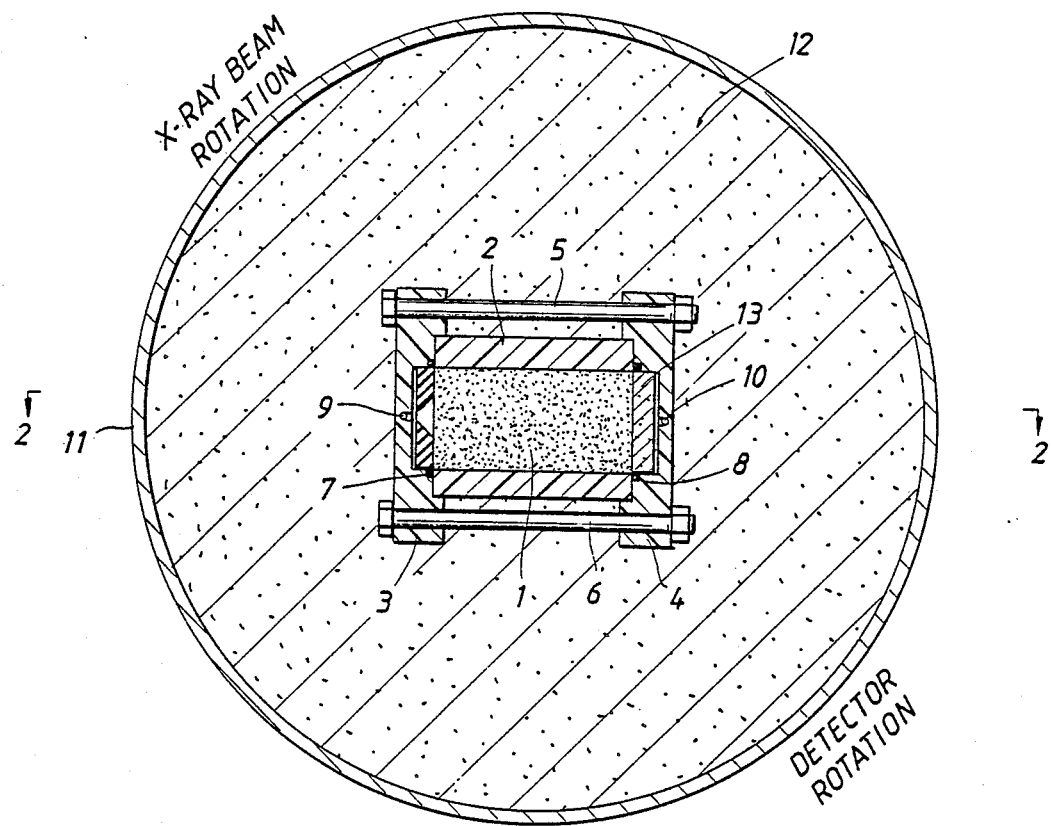
FIG. 1 depicts an apparatus suitable for employing the methods of the present invention.

In a preferred embodiment, methods and apparatus are provided for determining selected petrophysical properties of a material, such as capillary pressure curves and/or relative permeability, from information obtained by imaging the material. The methods of the present invention may be employed with any suitable imaging apparatus and may be employed for multiple phase flow in a material. The methods are initially described herein for a two-phase system; the equations for multiple-phase systems are more complicated but may easily be derived as described later herein. The apparatus is also described later herein.

For two-phase, incompressible, one-dimensional, immiscible flow with no gravity effects, Darcy's Law (see

*Porous Media-Fluid Transport and Pore Structure* F. A. L. Dullien, Academic Press, New York, 1979) for each phase is:

$$V_i = -\lambda_i \frac{\epsilon P_i}{\partial x}, \quad \lambda_i = \frac{k k_{ri}}{\mu_i}, \quad i = 1,2 \quad (1)$$

where x denotes the distance from the inflow end and k denotes the absolute permeability. For phase i, $\lambda_i$ denotes the mobility; $k_{ri}$, relative permeability; $\mu_i$, viscosity; $P_i$, pressure; and $V_i$, superficial velocity (which is the volumetric flow rate of fluid divided by the total area exposed to the fluid and not the interstitial pore velocities). The methods of the present invention may calculate mobilities from which relative permeabilities may be calculated, if absolute permeability and viscosity are known; absolute permeability and viscosity may be measured by other known methods. For example, absolute permeability and viscosity may be determined by any of the methods described in the Dullien reference cited hereinbefore.

Capillary pressure is defined as $$P_{21} = P_2 - P_1 \quad (2)$$

where subscript 2 refers to the non-wetting phase and subscript 1 to the wetting phase.

Differentiating equation (2) with respect to x, and then replacing the single phase differentials with equation (1), appropriately rearranged, followed by some manipulation and substitution, one obtains, $$V_1 = \frac{\lambda_1 V(t) + \lambda_1 \lambda_2 \frac{\partial P_{21}}{\partial x}}{\lambda_1 + \lambda_2} \quad (3)$$

$$V_2 = \frac{\lambda_2 V(t) - \lambda_1 \lambda_2 \frac{\partial P_{21}}{\partial x}}{\lambda_1 + \lambda_2} \quad (4)$$

where $V = V_1 + V_2$ denotes the total superficial velocity. The functional dependence of V only on time, t, stems from the continuity equation for incompressible flow.

The usual assumption that the core is homogeneous does not have to be made with this method; however, it is now introduced to simplify the following discussion. This allows capillary pressure and phase mobilities to be treated as functions only of saturation (in this case $S_1$, since $S_2 = 1 - S_1$). If the core is not homogeneous, then capillary pressure and phase mobilities are also dependent upon their spatial location; the methods of the present invention will still determine capillary pressure and phase mobilities for this inhomogeneous case also. However, when assumed homogeneous, the derivative appearing in Equation (3) or (4) may then, via the chain rule, be written as the product of the derivatives of the capillary pressure with respect to saturation and the saturation with respect to position. With this assumption, Equation (3) may be written as $$V_1(x,t) = f(S_1) V(t) + g(S_1) \frac{\partial S_1}{\partial x} \quad (5)$$

where $$f(S_1) = \frac{\lambda_1}{\lambda_1 + \lambda_2} \quad (6)$$

-continued $$g(S_1) = \frac{\lambda_1 \lambda_2}{\lambda_1 + \lambda_2} \frac{dP_{21}}{dS_1} \quad (7)$$

and $f(S_1)$ and $g(S_1)$ are herein defined as and referred to herein as mobility coefficients. $f(S_i)$ and $g(S_i)$ are selected petrophysical properties that may be determined by the methods of the present invention. These equations may be applied to any portion of a core sample that actually is homogeneous or any portion of a non-homogeneous sample that may be treated as if it is homogeneous. Thus, the entire core need not be homogeneous for use in the methods of the present invention.

Consider now what terms of Equation (5) may be actually measured in an imaging experiment. For example, in a CT experiment, the saturation profile may be directly measured as taught in copending U.S. Application No. 623,297 filed June 22, 1984, now U.S. Pat. No. 4,663,711, issued May 5, 1987, whose teachings are explicitly incorporated by reference herein; the derivative of saturation with respect to position and/or time may then be calculated based upon this saturation profile. In an NMR imaging experiment the saturation profile may be determined as taught in copending U.S. Application No. 881,160 filed July, 2, 1986, and now U.S. Pat. No. 4,769,602, issued Sept. 6, 1988, whose teachings are explicitly incorporated by reference herein; again the derivative of saturation with respect to position and/or time may be calculated based upon this saturation profile. Since the total superficial velocity, V, depends only on time it may be easily measured at either the inflow or outflow end of a sample. The superficial velocity of phase 1, $V_1$, is however, not measured directly but may be calculated from the continuity equation.

For incompressible flow, the continuity equation for phase i is $$\phi \frac{\partial S_i}{\partial t} + \frac{\partial V_i}{\partial x} = 0 \quad (8)$$

(where $\phi$ is porosity) which on integrating with respect to x gives $$V_i(x,t) = V_i^o(t) - \int_0^x \phi \frac{\partial S_i}{\partial t} dx \quad (9)$$

where, $V_i^o$ denotes the superficial velocity of phase i at $x=0$ and is, therefore, only a function of time. As with respect to distance, the derivative with respect to time in this equation can be calculated from the saturation information provided by the CT scanner, NMRI apparatus, or other imaging apparatus, as noted hereinbefore.

As noted hereinabove, V, may be measured directly and $V_1$ and $\partial S_i/\partial x$ may be easily calculated from saturation data, and substituted into equation (5). Therefore, by applying Equation (5) for a preselected saturation at two different points in the core, f and g may be calculated for this saturation. By doing this for all the saturations that occur in the core, the functional relationship of f and g upon saturation may be obtained directly, without having to make any assumptions about the form of this relationship. Of course, for a given saturation, Equation (5) may be applied for more than just two points in the core. In this case, multiple estimates of f and g may be obtained and, hence, a statistical estimate of their values may be obtained.

Knowledge of f allows calculation of only the ratios of the mobilities, or relative permeabilities; however, knowledge of g supplies additional information on the product $(\lambda_2)(\partial P_{21}/\partial S_1)$ from equation (7). By measuring pressure it is possible to obtain either $\lambda_1$ or $\lambda_2$; neither of these mobilities, $\lambda_1$ or $\lambda_2$ can be obtained directly or indirectly from only the saturation profiles. Saturations are measured as functions of x and t, but pressures may usually be obtained at only a limited number of pressure taps. One way to obtain $\lambda_1$ or $\lambda_2$ is to apply Equation (1) for two pressure taps spaced so closely together that the gradient in $P_i$ is measured directly. However, this is usually not easily accomplished.

More likely, the pressure taps are located at some distance from each other (perhaps at the core end faces). For two taps located at positions $x_1$ and $x_2$, Equation (1) may be integrated with respect to x to give:

$$\int_{x_1}^{x_2} \frac{V_i(x,t)}{\lambda_i(S_1)} dx = \Delta P_i(t) = P_i(x_1,t) - P_1(x_2,t) \qquad (10)$$

$V_i$ may be calculated by employing Equation (9); $S_1$ and $\Delta P$ may be measured directly. Equation (10) may then be solved for $\lambda_i$ by choosing several parametric forms for $\lambda_i$ and determining a least squares fit. One such parametric form may be, by way of example, but not limited to, $\lambda_i = aS^b$. Other appropriate mathematical methods other than a least squares fit may also be employed to fit the selected parametric form to equation (10).

Thus, either $\lambda_1$, or $\lambda_2$ may be determined from the selected mathematical fit to equation (10), depending upon whether $V_1$ or $V_2$ has been calculated from equation (9), as described hereinbefore. Once one $\lambda_i$ is known, the other may be calculated from $f(S_i)$; $f(S_i)$ is calculated from equation (5) at a preselected saturation at two different points in the core, as described hereinbefore.

The methods of the present invention may calculate mobilities from which relative permeabilities may be calculated from equation (1), if absolute permeability and viscosity are known; absolute permeability and viscosity may be measured by other known prior art methods. For example absolute permeability and viscosity may be determined by any of the methods described in the Dullien reference cited hereinbefore.

Once the mobilities are known, they may then be used with $g(S_i)$, obtained from equation (5) as described hereinbefore, to calculate the derivative of capillary pressure using equation (7). This derivative may then be integrated to obtain capillary pressure as a function of saturation.

Thus, the methods of the present invention may calculate $V_i$ from equation (9) and then apply equation (5) for at least two points for at least one preselected saturation in the core to calculate f and g, i.e. equations (6) and (7), respectively. Then equation (10) is used to determine $\lambda_i$. From $\lambda_i$ and $f(S_i)$ the other mobility is calculated. Then equation (7) is used to calculate the derivative of capillary pressure, which may then be integrated to provide capillary pressure as a function of saturation. Accordingly, the methods of the present invention may be employed to determine selected petrophysical properties, such as, but not limited to, mobility coefficients, mobilities, capillary pressure, and/or relative permeabilities.

However, for some applications, such as for example, but not limited to, reservoir modeling, it may only be necessary to determine f and g, so that no pressure measurement is required to be made.

In a similar manner, the methods of the present invention may be employed, in multiple-phase systems, as described hereinbelow.

For multiphase, incompressible, one-dimensional immiscible flow with no gravity effects, Darcy's Law for n phases is $$V_i = -\lambda_i \frac{\partial P_i}{\partial x}, \lambda_i = \frac{kk_{ri}}{\mu_i}, i = 1,2,\ldots,n \qquad (11)$$

where x denotes the distance from the inflow end and k denotes the absolute permeability. For phase i, $k_{ri}$ denotes relative permeability; $\lambda_i$, the mobility; $\mu_i$, viscosity; $P_i$, pressure; and $V_i$, superficial velocity, as noted hereinbefore.

The capillary pressure between the phases j and i is defined as $$P_{ji} = P_j - P_i \qquad (12)$$

Again, differentiating equation (12) with respect to x, employing equation (1) and with appropriate manipulation, one obtains, $$V_i = \frac{\lambda_i}{\lambda}\left[V(t) + \sum_{j=1}^{n} \lambda_j \frac{\partial P_{ji}}{\partial x}\right] \qquad (13)$$

where $V = V_1 + V_2 + \ldots V_n$ denotes the total superficial velocity and $\lambda = \lambda_1 + \lambda_2 + \ldots \lambda_n$ denotes the total mobility. The functional dependence of V on only time, t, stems from the continuity equation for incompressible flow as noted hereinbefore.

Again, the usual assumption that the core is homogeneous does not have to be made with this method; however, it is again introduced to simplify the discussion, as noted hereinbefore. This allows capillary pressure and phase mobilities to be treated as functions only of saturation.

Not all of the capillary pressures are independent. For n phases there are $n-1$ independent capillary pressures. This may be seen by writing $P_{ji} = P_{ni} - P_{nj}$. On rewriting the capillary pressures of Equation (13), with reference to phase n:

$$V_i = \frac{\lambda_i}{\lambda}\left[V(t) + \sum_{j=1}^{n} \lambda_j \left(\frac{\partial P_{ni}}{\partial x} - \frac{\partial P_{nj}}{\partial x}\right)\right] \qquad (14)$$

In general the capillary pressures $P_{nj}$ depend on $n-1$ saturations. Therefore, the chain rule may be used to obtain $$\frac{\partial P_{nj}}{\partial x} = \sum_{k=1}^{n-1}\left(\frac{\partial P_{nj}}{\partial S_k}\right)\left(\frac{\partial S_k}{\partial x}\right) \qquad (15)$$

Substituting this into Equation (14), gives:

$$V_i = f_i V(t) + \sum_{k=1}^{n-1} g_{ik} \frac{\partial S_k}{\partial x} \qquad (16)$$

where

-continued $$f_i = \frac{\lambda_i}{\lambda} \quad (17)$$

$$g_{ik} = \frac{\lambda_i}{\lambda} \sum_{j=1}^{n} \lambda_j \left[ \frac{\partial P_{ni}}{\partial S_k} - \frac{\partial P_{nj}}{\partial S_k} \right] \quad (18)$$

Note, $f_i$ and $g_{ik}$ are functions of $n-1$ saturations, and are defined herein as and referred to herein as mobility coefficients for multiple phases.

Consider now that terms of Equation (16) may be actually measured in an imaging experiment. In a CT scan experiment, the spatial saturation profile may be measured as noted hereinbefore; therefore, the derivative of saturation with respect to position may be calculated. Similarly for NMRI experiments, satuation profiles and their derivatives may be determined as noted hereinbefore. Since the total superficial velocity, v, depends only on time, it may easily be measured at the inflow or outflow end of the sample. The superficial velocity of phase i, $V_i$, is, however, not measured directly but calculated from the continuity equation.

For incompressible flow, the continuity equation for phase i is $$\phi \frac{\partial S_i}{\partial t} + \frac{\partial V_i}{\partial x} = 0, \text{ where } \phi \text{ is porosity}, \quad (19)$$

which on integrating with respect to x leads to $$V_i(x,t) = V_i^o(t) - \int_0^x \phi \frac{\partial S_i}{\partial t} dx \quad (20)$$

where, $V_i^o$ denotes the superficial velocity of phase i at $x=0$ and is, therefore, only a function of time. The derivative with respect to time in this equation may be calculated from the saturation information provided by the CT scanner, NMRI apparatus, or other imaging apparatus.

From Equation (16), $V_i$, V, and $\partial S_i/\partial x$ may either be measured directly or easily calculated from saturation data. There are $n-1$ independent equations for $V_i$. However, there are $n-1$ independent $f_i$ and $(n-1)^2$ independent $g_{ik}$ or $n(n-1)$ independent variables. Therefore, Equation (16) must be applied at least n times to obtain a solution for $f_i$ and $g_{ik}$. By applying Equation (16) for a preselected saturation at n positions or times, $f_i$ and $g_{ik}$ may be calculated at this saturation. By doing this for all the saturations that occur in the core, the direct functional relationship upon saturation may be obtained, without having to make any assumptions about the form of this relationship. Of course for a given saturation, Equation (16) may be applied for more than n points. For this case, multiple estimates of $f_i$ and $g_{ik}$ are obtained and, hence, a statistical estimate of their values may be obtained.

For two-phase flow it is possible to cover the whole saturation range in a single experiment. For example, a core initially filled with oil and connate water may be waterflooded to cover all oil saturations between the initial saturation and residual oil. Unfortunately, for multiphase flow not all saturations may be investigated in a single experiment. Further, because of capillary pressure hysteresis it is important to keep track of how saturations are reached. As an example of how this may be done, consider a three-phase gas drainage experiment. The core is initially filled with water and then oil flooded to an irreducible water saturation. Then water, or water and oil, are injected to reach an initial saturation in the imbibition mode. Gas is then injected at various imbibition initial conditions. Each experiment has a different set of initial conditions and will yield a different range of saturations over which $f_i$ and $g_{ik}$ may be measured.

As noted before, knowledge of $f_i$ allows calculation of only the ratios of the mobilities, or relative permeabilities; $g_{ik}$ supplies additional information on the product of mobilities and capillary pressure derivatives. Again one more piece of information is obtained from measuring pressure, as noted hereinbefore.

Any such pressure taps may be located some distance apart (perhaps at the core faces). For two taps located at positions $x_1$ and $x_2$, Equation (1) may be integrated with respect to x:

$$\int_{x_1}^{x_2} \frac{V_i(x,t)}{\lambda_i} dx = P_i(x_1, t) - P_i(x_2, t) = \Delta P_i(t) \quad (21)$$

$V_i$ may be calculated from Equation (20) while $\Delta P_i$ is measured directly. The equation may be solved for $\lambda_i$ by choosing a parametric form for $\lambda_i$ and determining a least squares or other mathematical technique fit, as noted hereinbefore in the two phase discussion.

Once $\lambda_i$ is known, the other $\lambda_i$'s may be determined (as noted hereinbefore for the two-phase example) from $f_i(S_i)$ and the known $\lambda_i$. Then the derivative of capillary pressure may be determined, as noted hereinbefore, from which the capillary pressure may be determined, as noted hereinbefore. Thus, the methods of the present invention may be employed with multiple fluids in a sample to determined selected petrophysical properties of the sample or fluids therein.

Figure 2:
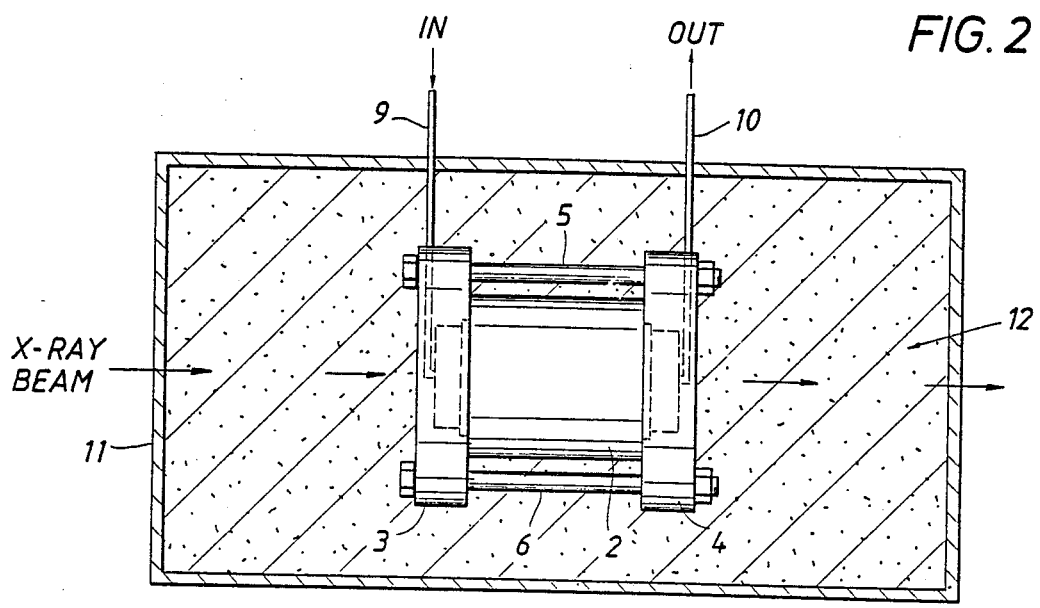
FIG. 2 depicts an alternate view of the apparatus depicted in FIG. 1.
Figure 3:
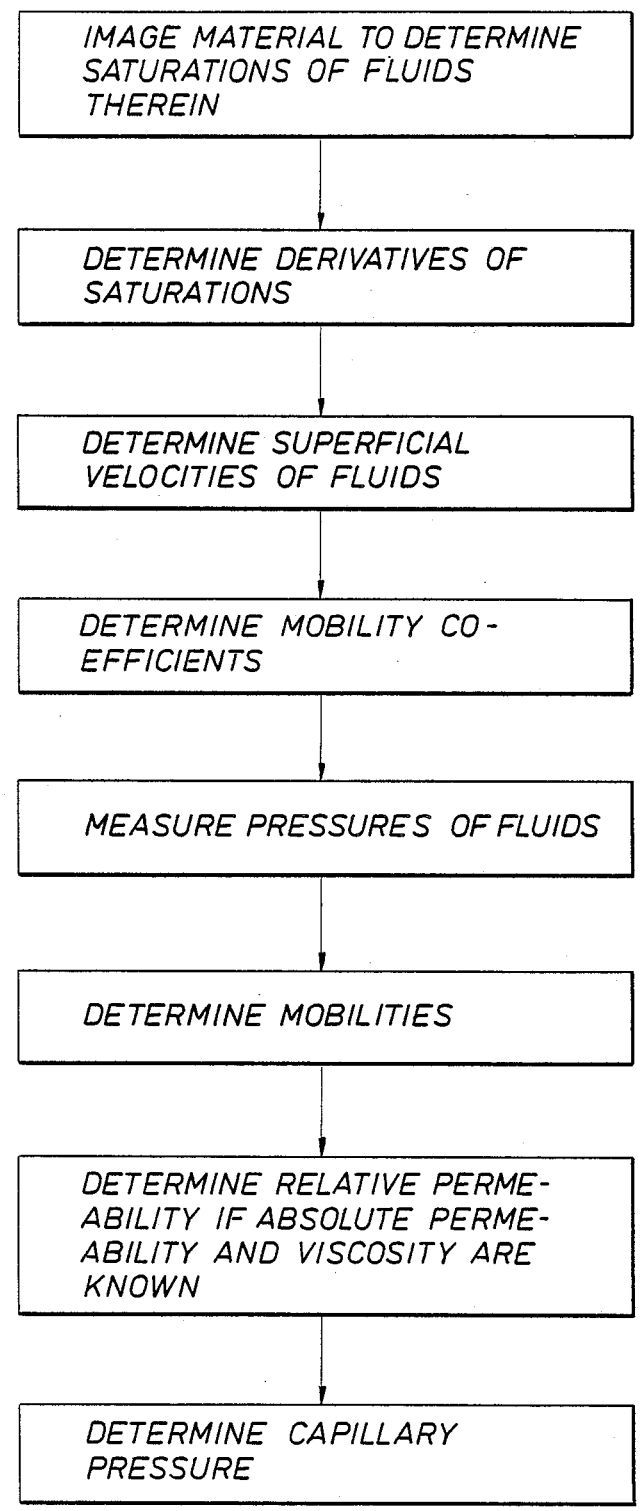
FIG. 3 depicts the steps of the method.

Referring now to FIGS. 1 and 2, there is shown a sample holder apparatus suitable for use with the methods of the present invention inside a CT scanner. The sample 1 is a cylindrical rod embedded in a lucite cylinder member 2. This is done either with epoxy or by heating the lucite to its softening point and pressing it onto the core's exterior circumference with hydrostatic pressure. The sample 1 is located so that its axis is contained within the plane of the X-rays, i.e. within the plane of the CT scanner gantry. The endpieces 3 and 4 are made from any low X-ray absorbing material, but perferably from polycarbonate for strength and low X-ray absorption. The endpieces 3 and 4 are pressed against the sample 1 by clamps 5 and 6 which are located outside the plane of the X-rays. The clamps may be constructed of any material, such as steel, since they are outside the plane of the X-rays. The clamps must supply sufficient force to overcome the oil pressure that is used in the measurement. O-ring seals 7 and 8 make fluid tight seals between endpieces 3 and 4 and lucite cylinder 2. Fluid flow tubing 9 and 10 made from nylon or TEFLON ® (a registered trademark of DuPont) or other tetrafluoroethylene polymers brings fluid to and from the sample 1.

One face of the core may be fitted with a thin piece of tissue paper (not shown) and butted against a capillary diaphragm 13 which may be sealed into endpiece 4 with epoxy. The use of capillary diaphragm 13 allows conventional relative permeability and/or capillary pressure experiments to be conducted and then be analyzed employing the methods of the present invention. Although a capillary diaphragm in one endpiece is a preferred embodiment of the apparatus of the present invention, the methods of the present invention may be employed without such a diaphragm; this may occur in any coreflood experiment where both capillary pressure and relative permeability play a role in the experiment. The methods of the present invention provide the most information when flow in a sample is influenced by both capillary pressure and relative permeability effects, rather than conventional experiments, which attempt to minimize the interactions between capillary pressure and relative permeability. For example, any slow rate core flood experiment may be easily analyzed with the methods of the present invention.

The capillary diaphragm 13 may be a porcelain frit or a Vycor frit which has a substantially high entry displacement pressure for the nonwetting phase. The displacement pressure of the frit should be higher than the highest capillary pressure to be measured in the core. The displacement pressure for a Vycor frit can be as high as 2000 psi.

Cylindrical member 2 may also have openings (not shown) disposed along its length to enable monitoring of pressure down the length of the sample, as discussed hereinbefore. These openings (not shown) may also contain appropriate material to avoid loss of fluids through these openings. Member 2 may also be modified to allow for overburden pressure to be placed on a sample.

In order to prevent X-ray beam hardening in the sample, the sample and holder and located inside a larger cylindrical housing 11. The cylindrical housing 11 is then filled with appropriate density material 12, such as grains of sand or limestone, so as to have approximately the same X-ray density as the sample. For example, a fine mesh Ottawa sand can be used to fill the housing if the sample is a sandstone. The sand grains may be ultrasonically vibrated to a high density to match a low porosity core. Alternatively, the housing may be filled with a liquid doped with X-ray absorber until it matches the core density. This assures that the X-ray path lengths through the object are equal for all CT projections.

One simple conventional example, analogous to primary drainage, for use of this apparatus is described hereinbelow. Other experiments may also be performed using this apparatus in accordance with the methods of the present invention. Accordingly, the apparatus and methods of the present invention are not limited to the specific example discussed hereinbelow.

The following discussion is intended only as a representative example of an operation of the apparatus. First, a core is inserted into the holder and is fully saturated with brine, then a doped oil phase is introduced at constant pressure through tubing 9. The oil phase may be for example iodated oil such as iodododecane. The oil pressure is below the displacement pressure for oil through capillary diaphragm 13 but sufficiently high to obtain high oil phase saturations in the core. The oil will displace the wetting phase (brine) through the capillary diaphragm 13 and the oil phase saturation will increase in the core. For early times after the oil pressure is increased, the oil phase propagates through the core. During this stage the measurement is most sensitive to the relative permeabilities of the oil and water. Once the oleic phase reaches the capillary diaphragm 13, the effect of capillary pressure becomes more important and the fluid saturations change rapidly near the capillary diaphragm 13. This stage of the displacement is most sensitive to the capillary pressure of the core. For very long times the fluid saturations in the core approach capillary equilibrium and the fluid saturations are spatially uniform through the core.

However, the methods of the present invention do not require for equilibrium to occur to determine capillary pressure. The methods of the present invention illustrate how to calculate capillary pressure at any time, since these methods account for the effect of relative permeability exactly. Thus, the methods of the present invention offer a faster way to measure capillary pressure, since equilibrium need not occur.

For NMR imaging the sample holder may be simplified because beam hardening is no longer a problem. Accordingly, the housing 11 and material 12 may no longer be required. In NMR imaging the entire sample holder must be inside the magnet, which places constraints on the material of clamps 5 and 6, which must now be constructed of non-magnetic and non-metallic parts such as fiberglass, S-glass, or Kevlar composites. Otherwise, the sample holder of FIG. 1 is satisfactory for NMR imaging as well.

Many other variations and modifications may be made in the methods and apparatus described hereinbefore by those having experience in this technology, without departing from the concepts of the present invention. Accordingly, it should be clearly understood that the methods and apparatus referred to in the foregoing description are illustrative only and are not intended as any limitations on the scope of the invention.

What is claimed is:

1. A method for determining at least one preselected petrophysical property of a material having determinable porosity parameters and determinable absolute permeability parameters and/or of preselected fluids having determinable viscosity parameters contained therein, comprising:
    imaging a preselected volume of such material to determine the saturations of such fluids in said preselected volume,
    determining time and spatial derivatives of said determined saturations
    determining superficial velocities of such fluids, and
    determining said at least one petrophysical property.

2. The method as described in claim 1, further comprising, measuring the pressures of at least one of such fluids, determining a second petrophysical property.

3. The method as described in claim 2, further comprising, determining at least a third petrophysical property from said first petrophysical property, said second petrophysical property, and said determinable parameters.

4. The method as described in claim 1, wherein said at least one petrophysical property comprises mobility coefficients, mobilities, relative permeabilities, capillary pressures, or any combinations thereof.

5. A method for determining mobilities of a sample of a material having a known porosity, comprising:
    providing said sample with at least two preselected fluids,
    imaging a preselected volume of said sample to determine the saturations of said fluids in said preselected volume,
    calculating time and spatial derivatives of said saturations,
    determining total superficial velocity for said fluids, determining the individual superficial velocities of said fluids from said porosity, said total superficial velocity, and said time derivatives, calculating mobility coefficients from said individual and total superficial velocities, saturations and spatial derivatives of saturations, measuring the differential pressures of one of said fluids, and calculating a mobility of one of said fluids from said pressures and individual superficial velocities.

6. A method for determining mobility coefficients of a sample of a material having a known porosity, comprising:

providing said sample with at least two preselected fluids, imaging a preselected volume of said sample to determine the saturations of said fluids in said preselected volume, calculating time and spatial derivatives of said saturations, determining total superficial velocity for said fluids, determining the individual superficial velocities of said fluids from said porosity, said total superficial velocity, and said time derivatives, and calculating said mobility coefficients from said individual and total superficial velocities, saturations and spatial derivatives of saturations.

7. A method for determining relative permeability of a sample of a material having a known porosity and absolute permeability, comprising:

providing said sample with at least two preselected fluids having known viscosities, imaging a preselected volume of said sample to determine the saturations of said fluids in said preselected volume, calculating time and spatial derivatives of said saturations, determining total superficial velocity for said fluids, determining the individual superficial velocities of said fluids from said porosity, said total superficial velocity, and said time derivatives, calculating mobility coefficients from said individual and total superficial velocities, saturations and spatial derivatives of saturations, measuring the differential pressures of one of said fluids, calculating a mobility of said one of said fluids from said pressures, and individual velocities, determining the mobilities of said other fluids from said mobility coefficients, and calculating relative permeabilities from said mobilities, viscosity and absolute permeability for said fluids.

8. A method for determining capillary pressure of a sample of a material having a known porosity and absolute permeability, comprising:

providing said sample with at least two preselected fluids, imaging a preselected volume of said sample to determine the saturations of said fluids in said preselected volume, calculating time and spatial derivatives of said saturations, determining total superficial velocity for said fluids, determining the individual superficial velocities of said fluids from said porosity, said total superficial velocity, and said time derivatives, calculating mobility coefficients from said individual and total superficial velocities, saturations and spatial derivatives of saturations, measuring the differential pressures of one of said fluids, calculating a mobility of said one of said fluids from said pressures, and individual superficial velocities, calculating the saturation derivatives of capillary pressures from said mobilities, and mobility coefficients for one of said fluids, and integrating said derivaties of capillary pressures to obtain said capillary pressures.

9. The method of claim 1, wherein said at least one petrophysical property is determined based upon statistical techniques.

* * * * *